(12) United States Patent
Hauf et al.

(10) Patent No.: US 11,345,910 B2
(45) Date of Patent: May 31, 2022

(54) MODIFIED MUSSEL PROTEINS, USES THEREOF AND RELATED COMPOUNDS

(71) Applicant: Technische Universität Berlin, Berlin (DE)

(72) Inventors: Matthias Hauf, Berlin (DE); Nediljko Budisa, Feldkirchen (DE); Florian Richter, Cologne (DE); Tobias Baumann, Berlin (DE); Tobias Schneider, Berlin (DE)

(73) Assignee: Technische Universität Berlin, Berlin (DE)

( * ) Notice: Subject to any disclaimer, the term of this patent is extended or adjusted under 35 U.S.C. 154(b) by 77 days.

(21) Appl. No.: 16/498,438

(22) PCT Filed: Mar. 26, 2018

(86) PCT No.: PCT/EP2018/057641
§ 371 (c)(1),
(2) Date: Sep. 27, 2019

(87) PCT Pub. No.: WO2018/178013
PCT Pub. Date: Oct. 4, 2018

(65) Prior Publication Data
US 2021/0087237 A1    Mar. 25, 2021

(30) Foreign Application Priority Data

Mar. 28, 2017   (EP) .................................... 17163362

(51) Int. Cl.
*C12N 9/00*     (2006.01)
*C07K 14/435*   (2006.01)

(52) U.S. Cl.
CPC .......... *C12N 9/93* (2013.01); *C07K 14/43504* (2013.01); *C12Y 601/01014* (2013.01)

(58) Field of Classification Search
CPC ........................... C12N 9/93; C07K 14/43504
See application file for complete search history.

(56) References Cited

U.S. PATENT DOCUMENTS 5,202,236 A    4/1993 Maugh et al.
10,449,267 B2  10/2019 Lu et al.
(Continued)

FOREIGN PATENT DOCUMENTS

JP    2008504016 A    2/2008
WO    2006034410 A2   3/2006
(Continued)

OTHER PUBLICATIONS

Budisa. Expanding the DOPAUniverse with Genetically Encoded, Mussel-Inspired Bioadhesives for Material Sciences and Medicine. ChemBioChem 2019, 20, 2163-2190.*
(Continued)

*Primary Examiner* — Yong D Pak
(74) *Attorney, Agent, or Firm* — The Webb Law Firm

(57) ABSTRACT

Disclosed is a mussel adhesive protein including at least one photocaged 3,4-dihydroxyphenylalanine derivative residue including a protecting group on at least one hydroxyl residue of its catechol moiety. The photocaged 3,4-dihydroxyphenylalanine derivative residue replaces a naturally occurring amino acid and the protecting group can be cleaved from the 3,4-dihydroxyphenylalanine derivative residue by irradiation with UV light.

10 Claims, 5 Drawing Sheets

Specification includes a Sequence Listing.

(56) References Cited

U.S. PATENT DOCUMENTS

| | | |
|---|---|---|
| 2006/0134746 A1 | 6/2006 | Deiters et al. |
| 2008/0227205 A1 | 9/2008 | Cho |
| 2009/0151600 A1 | 6/2009 | Cha et al. |
| 2009/0227002 A1 | 9/2009 | Schultz et al. |

FOREIGN PATENT DOCUMENTS

| | | |
|---|---|---|
| WO | 2006132969 A2 | 12/2006 |
| WO | 2015126480 A2 | 8/2015 |
| WO | 2016210350 A1 | 12/2016 |

OTHER PUBLICATIONS

Yang. In Vivo Residue-Specific Dopa-Incorporated Engineered Mussel Bioglue with Enhanced Adhesion and Water Resistance. Angewandte Chemi, 2014, pp. 13360, vol. 53, No. 49 and Supporting Information pp. 1-13.*
Arbely et al., "Photocontrol of Tyrosine Phosphorylation in Mammalian Cells via Genetic Encoding of Photocaged Tyrosine", Journal of the American Chemical Society, 2012, pp. 11912-11915, vol. 134, No. 29.
Danner et al., "Adhesion of Mussel Foot Protein Mefp-5 to Mica: An Underwater Superglue", Biochemistry, 2012, pp. 6511-6518, vol. 51, No. 33.
Deiters et al., "A Genetically Encoded Photocaged Tyrosine", Angewandte Chemie (International Edition in English), 2006, pp. 2728-2731, vol. 45, No. 17.
Donkerwolcke et al., "Tissues and bone adhesives—historical aspects", Biomaterials, 1998, pp. 1461-1466, vol. 19, No. 16.
Ebner et al., "A New, Simple Method for Linking of Antibodies to Atomic Force Microscopy Tips", Bioconjugate Chemistry, 2007, pp. 1176-1184, vol. 18.
Fichman et al., "Seamless Metallic Coating and Surface Adhesion of Self-Assembled Bioinspred Nanostructures Based on Di-(3,4-dihydroxy-L-phenylalanine) Peptide Motif", ACS Nano, 2015, p. 7220-7228, vol. 8, No. 7.
Hauf et al., "Photoactivatable mussel-based underwater adhesive proteins by an expanded genetic code", Chembiochem, 2017, pp. 1819-1823, vol. 18, No. 18.
Hoffman et al., "Characterisation of a new bioadhesive system based on polysaccharides with the potential to be used as bone glue", Journal of Materials Science: Materials in Medicine, 2009, pp. 2001-2009, vol. 20, No. 10.
Hwang et al., "Practical recombinant hybrid mussel bioadhesive fp-151", Biomaterials, 2007, pp. 3560-3568, vol. 28, No. 24.
Johnson et al., "RF1 knockout allows ribosomal incorporation of unnatural amino acids at multiple sites", Nature Chemical Biology, 2011, pp. 779-786, vol. 7, No. 11.
Lajoie et al., "Genomically Recoded Organisms Expand Biological Functions", Science, 2013, pp. 357-360, vol. 342, No. 6156.
Larregola et al., "Congeneric bio-adhesive mussel foot proteins designed by modified prolines revealed a chiral bias in unnatural translation", Biochemical and Biophysical Research Communications, 2012, pp. 646-650, vol. 421.
Lee et al., "Mussel-Inspired Surface Chemistry for Multifunctional Coatings", Science, 2007, pp. 426-430, vol. 318, No. 5849.
Lee et al., "Mussel-Inspired Adhesives and Coatings", Annual Review of Materials Research, 2011, pp. 99-132, vol. 41.
Liu et al., "Adding New Chemistries to the Genetic Code", Annual Review of Materials Research, 2010, pp. 413-444, vol. 79.
Luo et al., "Genetically encoded optical activation of DNA recombination in human cells", Chemical Communications (Cambridge, England), 2016, pp. 8529-8532, vol. 52, No. 55.
Montanaro et al., "Cytotoxicity, blood compatibility and antimicrobial activity of two cyanoacrylate glues for surgical use", Biomaterials, 2001, pp. 59-66, vol. 22, No. 1.
Nguyen et al., "Genetic Encoding of Photocaged Cysteine Allows Photoactivation of TEV Protease in Live Mammalian Cells", Journal of the American Chemical Society, 2014, pp. 2240-2243, vol. 136, No. 6.
Paz et al., "Specific Detection of Quinoproteins by Redox-cycling Staining", The Journal of Biological Chemistry, 1991, pp. 689-692, vol. 266, No. 2.
Richter et al., "A combined computational/high-throughput screening approach to redesign AA-tRNA synthetase specificity", 2016, 1 page.
Shafiq et al., "Bioinspired Underwater Bonding and Debonding on Demand", Angewandte Chemie (International Edition in English), 2012, pp. 4332-4335, vol. 51, No. 8.
Shi et al., "One-Pot UV-Triggered o-Nitrobenzyl Dopamine Polymerization and Coating for Surface Antibacterial Application", ACS Applied Materials & Interfaces, 2016, pp. 33131-33138, vol. 8, No. 48.
Silverman et al., "Understanding Marine Mussel Adhesion", Marine Biotechnology, 2007, pp. 661-681, vol. 9, No. 6.
Soloshonok et al., "Efficient and Practical Protection of the Catechol Residue of 3,4-Dihydroxy-phenylalanine (DOPA) Derivative as Acetonide", Synthesis, 2008, pp. 693-695, No. 5.
Stewart, "Protein-based underwater adhesives and the prospects for their biotechnological production", Applied Microbiology and Biotechnology, 2011, pp. 27-33, vol. 89, No. 1.
Stewart et al., "Natural Underwater Adhesives", Journal of Polymer Science Part B: Polymer Physics, 2011, pp. 757-771, vol. 49, No. 11.
Waite, "Reverse Engineering of Bioadhesion in Marine Mussels", Annals New York Academy of Sciences, 1999, pp. 301-309.
Weber et al., "Adhesives in Orthopaedic Surgery A Review of the Literature and In Vitro Bonding Strengths of Bone-bonding Agents", Clinical Orthopaedics and Related Research, 1984, pp. 249-261, No. 191.
Wilding et al., "Linking of Sensor Molecules with Amino Groups to Amino-Functionalized AFM Tips", Bioconjugate Chemistry, 2011, pp. 1239-1248, vol. 22, No. 6.
Wilkins et al., "Site-Specific Incorporation of Fluorotyrosines into Proteins in *Escherichia coli* by Photochemical Disguise", Biochemistry, 2010, pp. 1557-1559, vol. 49, No. 8.
Young et al., "An Enhanced System for Unnatural Amino Acid Mutagenesis in *E. coli*", Journal of Molecular Biology, 2010, pp. 361-374, vol. 395, No. 2.
Yu et al., "Mussel protein adhesion depends on thiol-mediated redox modulation", Nature Chemical Biology, 2011, pp. 588-590, vol. 7, No. 9.
"Orthogonal aminoacyl tRNA synthetase mutant p-NH2-PheRS(3a)", EBI Accession No. GSP: ABP71806.
"JP 2014161229-A/2: Method for Regulation of Protein Expression", Database JPO Proteins, 2014, 1 page.
Nishida, Jin et al., "XV. New development of green material (9) Adhesive protein-mimic polymeric material, Catechol based polymer—Mussel Adhesive Protein Mimetic Polymer.", Journal of the Adhesion Society of Japan, 2013, pp. 389-395, vol. 49, No. 10. (relevant for the reasons noted in English translation of the JP OA).

\* cited by examiner

MODIFIED MUSSEL PROTEINS, USES THEREOF AND RELATED COMPOUNDS

CROSS-REFERENCE TO RELATED APPLICATIONS

This application is the United States national phase of International Application No. PCT/EP2018/057641 filed Mar. 26, 2018, and claims priority to European Patent Application No. 17 163 362.1 filed Mar. 28, 2017, the disclosures of which are hereby incorporated by reference in their entirety.

The Sequence Listing associated with this application is filed in electronic format via EFS-Web and is hereby incorporated by reference into the specification in its entirety. The name of the text file containing the Sequence Listing is 1907026_ST25.txt. The size of the text file is 28,957 bytes, and the text file was created on Sep. 23, 2019.

BACKGROUND OF THE INVENTION

Field of the Invention

The disclosure relates to a modified mussel protein, to a nucleic acid encoding for such a modified mussel protein, and to an aminoacyl-tRNA synthetase suited for manufacturing such a modified mussel protein.

Description of Related Art

In medicine, there is a long-standing demand for biocompatible glues, which can be applied for the treatment of bone fractures or accelerated wound healing in order to replace currently existing, limited therapeutic approaches, which make use of pins and nails.[1] Biocompatible bio-glues must meet several demands, such as good binding strength to the tissue (adhesion), a high stability under physiological, wet conditions (cohesion), controllable biodegradability, no immunogenicity in the organism as well as no toxicity.[2] However, a bio-glue that meets these demands is currently not available. While bio-glues like fibrin show weak binding strength and rapid biodegradation, synthetic glues like cyanoacrylates show strong binding properties, but are potentially toxic for organisms[3] and not absorbable, thus impairing endogenous bone repair.[1]

A biological glue that can meet the above stated requirements is found in marine mussels, which are able to affix themselves to solid surfaces underwater in intertidal zones by means of their protein-based glue.[4,5] In order to enable adhesion, mussels fabricate the so-called byssus, which consists of several proteinaceous threads, which end in an adhesive plaque. The adhesive plaque is in direct contact with the surface and is composed of different mussel adhesive proteins (MAPs), which allow for a strong, permanent adhesion on a variety of organic and inorganic surfaces. The tensile strength is up to 10 MPa[6], which is in the range of cancellous bones (around 5 MPa).[7] They key player of underwater adhesion is the catecholic amino acid 3,4-dihydroxyphenylalanine (Dopa), which is formed post-translationally from tyrosine. Dopa contributes to adhesion by various mechanisms such as hydrogen bonding, metal coordination or quinone-mediated crosslinking.[4] Reflecting the high importance of Dopa for mussel adhesion, MAPs feature high Dopa contents of up to 30 mol %.

Due to low extraction yields from mussels, much effort has been made to synthesize mussel-inspired polymers[8,9] or to recombinantly produce MAPs[10,11] by making use of an enzymatic in vitro hydroxylation step, co-expression of tyrosinase or by making use of eukaryotic expression systems in order to hydroxylate tyrosine residues post-translationally. While these approaches suffer from low binding strengths, low hydroxylation efficiencies or low protein yields, respectively, residue-specific replacement of tyrosine with Dopa[11] has been conducted in E. coli more recently by exploiting the substrate tolerance of E. coli Tyrosyl tRNA synthetase (TyrRS). This approach, however, suffers from the poor activation rate of Dopa by E. coli TyrRS, as well as impaired cell growth due to proteome-wide incorporation of Dopa.

SUMMARY OF THE INVENTION

It is an object underlying the proposed solution to provide a novel system and suited tools for producing Dopa-containing proteins, in particular Dopa-containing mussel proteins, as well as providing accordingly modified mussel proteins themselves.

This object is achieved, amongst others, by a modified mussel protein having features as described herein. Such a mussel protein comprises at least one 3,4-dihydroxyphenylalanine derivative residue instead of a naturally occurring amino acid in the respective native analogue of the modified mussel protein (e.g., a natural occurring mussel protein). Thereby, the 3,4-dihydroxyphenylalanine derivative residue comprises a protecting group on at least one hydroxyl residue of its catechol moiety. It can also be denoted as protected 3,4-dihydroxyphenylalanine derivative residue.

The modified mussel protein is, in an embodiment, a modified mussel adhesive protein. In the following, the term "modified mussel proteins" always encompasses modified mussel adhesive proteins and could be limited to this embodiment.

The 3,4-dihydroxyphenylalanine derivative residue is a photocaged 3,4-dihydroxyphenylalanine derivative residue. The protecting group can be cleaved from the 3,4-dihydroxyphenylalanine derivative residue by irradiation with UV light.

In an embodiment, the modified mussel adhesive protein is a modified fp-5 protein (MAP fp-5).

In an embodiment, the only modification of the photocaged 3,4-dihydroxyphenylalanine derivative as compared to 3,4-dihydroxyphenylalanine is the protecting group on at least one hydroxyl residue of its catechol moiety. In another embodiment, the 3,4-dihydroxyphenylalanine derivative additionally lacks an amino group in C2 position.

In an embodiment, the protecting group is chemically bound to both hydroxyl residues of the catechol moiety. Alkyl chains having 1, 2, 3, 4, 5, 6, 7, 8, 9 or 10 carbon atoms are particularly suited for this purpose.

A suited example of a protecting group is 6-nitro-1,3-benzodioxol. This protecting group has been described to undergo a fast decaging process when irradiated with light having a wavelength of 365 nm. Furthermore, undesired intracellular reduction of the nitro group to an amine was not observed for the 1-nitro-3,4-methylenedioxybenzene group, thus improving the overall efficiency of decaging. Consequently, this protecting group is very well suited in order to produce photocaged Dopa to be incorporated into a modified mussel protein. The chemical structure of this protecting group is indicated in the following, wherein R is, in the instant embodiment, a Dopa derivative residue or a Dopa residue:

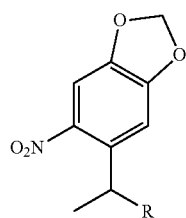

In an embodiment, the protecting group is chemically bound to one hydroxyl residue of the catechol moiety.

In an embodiment, ortho-nitrobenzyl is used as UV-cleavable protecting group so that the photocaged 3,4-dihydroxyphenylalanine derivative is ortho-nitrobenzyl-3,4-dihydroxyphenylalanine (ONB-Dopa).

The ortho-nitrobenzyl group (ONB group)[12] is a protecting group that can be readily cleaved off by irradiation with UV light at 365 nm, thus releasing the catecholic functionality of Dopa.

The ONB group has been frequently used to produce caged proteins which can be activated by simple irradiation with UV light. While similar compounds such as ONB-tyrosine[12-14] and ONB-fluorotyrosine[15] have been described, ONB-Dopa was, to the knowledge of the inventors, not used in any study before. The advantages of photoprotected Dopa analogues are that it allows the production of photoactivatable bio-glues, and avoids Dopa autoxidation to Dopaquinone, which has been described to impair adhesive properties.[16]

In order to synthesise the modified mussel protein, the inventors established a system of novel aminoacyl-tRNA synthetases (aaRS) and a cognate tRNA. In recent years, orthogonal pairs (o-pairs) consisting of an aaRS and the cognate tRNA have been engineered in order to allow activation and incorporation of non-canonical amino acids (ncAA) into proteins in response to the amber stop codon.[17] The same approach has been taken here. The used tRNA recognizes the amber stop codon (TGA) that, consequently, no longer acts as stop codon but as codon coding for an amino acid loaded to the specific tRNA. This amino acid is determined by the newly developed aminoacyl-tRNA synthetases and is in the instant case ONB-Dopa. Modifications of the o-pair would allow for incorporation of other photocaged 3,4-dihydroxyphenylalanine derivative residues.

The novel aaRS allow the incorporation of ONB-Dopa into proteins at multiple sites leading to the production of caged mussel proteins, whose adhesive properties can be activated spatiotemporally upon irradiation at 365 nm. These light-activatable (photoactivatable) mussel proteins hold great potential for biomedical purposes, e.g., for the treatment of bone fractures.

As the cooperative effect of multiple Dopa residues strongly improves mussel adhesion, several photocaged 3,4-dihydroxyphenylalanine derivative residues, in particular ONB-Dopa residues, are incorporated simultaneously into the modified mussel protein in an embodiment in order to mimic the adhesive abilities of mussels. Thus, in an embodiment, the modified mussel protein comprises 2, 3, 4, 5, 6, 7, 8, 9, 10, 11, 12, 13, 14, 15, 16, 17, 18, or 19 of such photocaged 3,4-dihydroxyphenylalanine derivative residues, in particular ONB-Dopa residues. In an embodiment, it comprises 2 to 19 according residues, in particular 3 to 18, in particular 4 to 17, in particular 5 to 16, in particular 6 to 15, in particular 7 to 14, in particular 8 to 13, in particular 9 to 12, in particular 10 to 11 according residues.

In an embodiment, the photocaged 3,4-dihydroxyphenylalanine derivative residue, in particular the ONB-Dopa residue, replaces a tyrosine residue. To produce an accordingly modified mussel protein, at least one codon coding for tyrosine is genetically replaced by the amber stop codon, which is then used by the newly developed orthogonal pair of an aaRS and a cognate tRNA for introducing ONB-Dopa or another photocaged 3,4-dihydroxyphenylalanine derivative residue during protein synthesis into the modified mussel protein.

In an embodiment, the modified mussel protein comprises an amino acid sequence being at least 95%, in particular at least 96%, in particular at least 97%, in particular at least 98%, in particular at least 99%, in particular at least 99.5% and very particular 100% identical to SEQ ID NO: 1, SEQ ID NO: 2, SEQ ID NO: 3, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, or SEQ ID NO: 19.

SEQ ID NO: 1 describes a modified mussel protein bearing 5 ONB-Dopa residues. SEQ ID NO: 2 describes a modified mussel protein bearing 10 ONB-Dopa residues. SEQ ID NO: 3 describes a modified mussel protein bearing 19 ONB-Dopa residues, i.e. all 19 tyrosine residues of the wild type mussel protein (fp-5) are exchanged by ONB-Dopa. SEQ ID NO: 11, SEQ ID NO: 12 and SEQ ID NO: 13 are identical to the first 77 amino acids of SEQ ID NO: 1, SEQ ID NO: 2, or SEQ ID NO: 3, respectively, but do not contain a C-terminal His$_6$ tag. In an embodiment, the modified mussel protein does not only comprise such an amino acid sequence, but consists of this amino acid sequence.

SEQ ID NO: 14 describes a modified mussel protein bearing 5 photocaged Dopa residues (ONB-Dopa and 6-nitro-1,3-benzodioxol-Dopa are examples of a photocaged Dopa residue). SEQ ID NO: 15 describes a modified mussel protein bearing 10 photocaged Dopa residues. SEQ ID NO: 16 describes a modified mussel protein bearing 19 photocaged Dopa residues, i.e. all 19 tyrosine residues of the wild type mussel protein (fp-5) are exchanged by photocaged Dopa residues. SEQ ID NO: 17, SEQ ID NO: 18 and SEQ ID NO: 19 are identical to the first 77 amino acids of SEQ ID NO: 14, SEQ ID NO: 15, or SEQ ID NO: 16, respectively, but do not contain a C-terminal His$_6$ tag. In an embodiment, the modified mussel protein does not only comprise such an amino acid sequence, but consists of this amino acid sequence.

In an embodiment, the modified mussel protein comprises an amino acid sequence being at least 95%, in particular at least 96%, in particular at least 97%, in particular at least 98%, in particular at least 99%, in particular at least 99.5% and very particular 100% identical to SEQ ID NO: 4 that is fused to the N-terminus of the amino acid sequence as defined in the preceding three paragraphs. The protein having SEQ ID NO: 4 is a maltose-binding protein (MBP) having a Tobacco Etch Virus (TEV) protease cleavage site and can also be denoted as MBP-TEV. It can be easily cleaved from the protein to which it is fused by treating it with TEV protease. After such treatment, a protein having an amino acid sequence being at least 95% identical to SEQ ID NO: 1, SEQ ID NO: 2, SEQ ID NO: 3, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, or SEQ ID NO: 19 results.

In an aspect, the solution relates to the use of the modified mussel protein according to the preceding explanations as a biodegradable glue, in particular to an according in vitro use.

In an aspect, the solution relates to a method for combining two elements by gluing them together with a biodegradable glue comprising a modified mussel protein according to the preceding explanations.

In an aspect, the solution relates to the use of the modified mussel protein according to the preceding explanations for coating a surface with a functional entity that is covalently bound to the modified mussel protein. Thereby, the solution particularly relates to an according in vitro use. By such a use of the modified mussel protein, the surface properties of many different substrates can be adjusted in any desired way by choosing an appropriate functional entity. The functional entity can be, e.g., a peptide or a protein.

In an embodiment, the functional entity exhibits antimicrobial properties. In this embodiment, it is possible to establish an antimicrobial surface coating of an article. To give an example, an implant like a prosthesis or another medical article can be coated by an according functionalized modified mussel protein. Thereby, an antimicrobial peptide is very well suited to be fused with the modified mussel protein.

In an aspect, the solution relates to a method for coating the surface of an article with a functionalized modified mussel protein comprising the modified mussel protein according to the preceding explanations and a functional entity being covalently bound to the modified mussel protein.

In an aspect, the solution relates to the use of a modified mussel protein according to the preceding explanations in medicine, In particular in surgery or therapy (first medical use). In another aspect, the solution relates to the use of the modified mussel protein according to the preceding explanations in surgery or therapy as biodegradable glue.

In an aspect, the solution relates to a therapeutic method for tightly connecting two parts of the body of a human or an animal in need thereof by applying a biodegradable glue comprising a modified mussel protein according to the preceding explanations to at least one of the parts to be connected, in particular to both parts to be connected.

In an aspect, the solution relates to the use of the modified mussel protein according to the preceding explanations in the treatment of a bone fracture or for enhancing wound healing (second or further medical use). Wound healing can be enhanced, e.g., by coupling the modified mussel protein with an antimicrobial entity such as an antimicrobial peptide and by applying this functionalized modified mussel protein onto or into a wound to prevent or ameliorate wound infection. For this purpose, the functionalized modified mussel protein can be applied onto a dressing that is intended to be used for wound treatment.

In an aspect, the solution relates to a method of treating a bone fracture or a method for enhancing wound healing by applying a modified mussel protein according to the preceding explanations to a human or animal in need thereof, in particular by applying such a modified mussel protein onto a fractured bone or onto a wound that is to be healed.

All described uses and all corresponding methods can be particularly well applied after the corresponding modified mussel protein is activated by UV light, in particular with UV light having a wavelength of 360 to 370 nm, in particular 365 nm, so as to cleave the ONB protecting group and to expose the Dopa residues.

In an aspect, the solution relates to a nucleic acid encoding for a modified mussel protein according to the preceding explanations, having a sequence being at least 99%, in particular at least 99.5%, in particular 100% identical to SEQ ID NO: 5, SEQ ID NO: 6 or SEQ ID NO: 7. The nucleic with SEQ ID NO: 5 comprises 5 TAG triplets that are recognized by a specific tRNA that is loaded by a specific aminoacyl-tRNA synthetase with ONB-Dopa. Thus, these TAG triplets serve for incorporating ONB-Dopa during protein synthesis into the modified mussel protein to be synthesized. Thus, this nucleic acid encodes for the modified mussel protein according to SEQ ID NO: 1. The nucleic with SEQ ID NO: 6 comprises 10 TAG triplets; it encodes for the modified mussel protein according to SEQ ID NO: 2. The nucleic with SEQ ID NO: 7 comprises 19 TAG triplets; it encodes for the modified mussel protein according to SEQ ID NO: 3. In each case, the TAG triplets replace a triplet encoding for tyrosine in the underlying unmodified mussel protein.

In an aspect, the solution relates to an aminoacyl-tRNA synthetase, comprising an amino acid sequence being at least 98%, in particular at least 99%, in particular at least 99.5%, in particular 100% identical to SEQ ID NO: 8, SEQ ID NO: 9 or SEQ ID NO: 10. In an embodiment, the aminoacyl-tRNA synthetase consists of an according amino acid sequence. The protein according to SEQ ID NO: 8 can also be referred to as ONB-DopaRS-1, the protein according to SEQ ID NO: 9 can also be referred to as ONB-DopaRS-2, and the protein according to SEQ ID NO: 10 can also be referred to as ONB-DopaRS-3. Such an aminoacyl-tRNA synthetase is able to load a corresponding tRNA with ONB-Dopa. Thus, it is very well suited to be used for incorporating ONB-Dopa into a peptide to be synthesized. Since the substrate binding site of an aminoacyl-tRNA synthetase comprises ca. 30 amino acids, $20^{30} \approx 10^{39}$ possible sequences result. It was a very surprising finding for the inventors to identify three different (but closely related) aminoacyl-tRNA synthetases that are very well suited to load a cognate tRNA with ONB-Dopa.

The solution relates in an aspect to the use of an aminoacyl-tRNA synthetase according to the preceding paragraph for incorporating ortho-nitrobenzyl-3,4-dihydroxyphenylalanine into a peptide to be synthetized. Thereby, the term "peptide" relates within the instant disclosure to any of dipeptides, oligopeptides, polypeptides and proteins. In an embodiment, the aminoacyl-tRNA synthetase is used for incorporating ONB-Dopa into a protein to be synthesized. The synthesis can take place in bacteria, in yeast cells, in plant cells, in whole plants or in a cell-free protein synthesis system.

According to the knowledge of the inventors, photocaged 3,4-dihydroxyphenylalanine derivative residues such as ONB-Dopa have not been used for synthesizing peptides. The solution relates, therefore, in an aspect to the use of photocaged 3,4-dihydroxyphenylalanine derivative residue, in particular of ONB-Dopa, in the synthesis of peptides. Regarding the meaning of the term "peptide" and suited synthesis systems, reference is made to the preceding paragraph.

ONB-Dopa can be present into stereoisomeric forms, namely the D form and the L form. In an embodiment, the ONB-Dopa is ONB-L-Dopa. This embodiment is explicitly applicable to the protein sequences disclosed in the instant application in which ONB-Dopa is present.

The ONB group can be bound to Dopa in meta (m) or para (p) position. In an embodiment, the ONB-Dopa is m-ONB-Dopa, in particular m-ONB-L-Dopa. This embodiment is also explicitly applicable to the protein sequences disclosed in the instant application in which ONB-Dopa is present.

The chemical structure of m-ONB-L-Dopa corresponds to formula (I) and the chemical structure of ONB-L-Dopa derivable from m-ONB-L-Dopa by UV irradiation corresponds to formula (II):

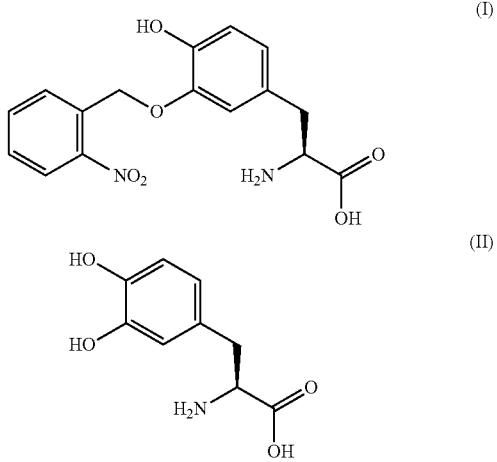

In a further aspect, the solution relates to a method for producing a modified mussel protein according to the preceding explanations. This manufacturing method is characterized by the steps explained in the following.

First, a genetically modified nucleic acid sequence encoding for the modified mussel protein to be synthesized is provided. Thereby, this modified nucleic acid sequence contains one or more amber stop codons (TAG triplets) instead of naturally occurring triplets at the same site of the nucleic acid. In an embodiment, a triplet coding for tyrosine (a TAT or TAC triplet) has been replaced by a TAG triplet.

In an embodiment, a nucleic acid sequence being at least 99%, in particular at least 99.5%, in particular 100% identical to SEQ ID NO: 5, SEQ ID NO: 6 or SEQ ID NO: 7 can be provided.

Afterwards, protein synthesis is carried out by using the provided nucleic acid as template. This protein synthesis can, e.g., be carried out in bacteria, in yeast cells, in plant cells, in whole plants or in a cell-free protein synthesis system. Thereby, the system used for protein synthesis comprises an orthogonal pair of a specific aminoacyl-tRNA synthetase as well as a corresponding tRNA. Thereby, the aminoacyl-tRNA synthetase is capable of transferring a photocaged 3,4-dihydroxyphenylalanine derivative residue, in particular ONB-Dopa, onto the corresponding tRNA. This purpose—in particular if ONB-Dopa is chosen as photocaged 3,4-dihydroxyphenylalanine derivative residue—can best be achieved if the aminoacyl-tRNA synthetase comprises or consists of an amino acid sequence being at least 98%, in particular at least 99%, in particular at least 99.5%, in particular 100% identical to SEQ ID NO: 8, SEQ ID NO: 9 or SEQ ID NO: 10.

A suited tRNA to be used for incorporating ONB-Dopa into the modified mussel protein to be synthesized is a tRNA previously described in literature.[23] The protein synthesis system further comprises "usual" amino acid tRNA-synthetases and corresponding tRNAs for performing proper protein synthesis.

The synthesized modified mussel protein can then be purified by a technique generally known to a person skilled in the art such as using an agarose resin, magnetic beads or suited columns. Thereby, a Hiss tag can well be used for purification purposes (see, e.g., SEQ ID NO: 1, SEQ ID NO: 2, SEQ ID NO: 3, SEQ ID NO: 14, SEQ ID NO: 15, or SEQ ID NO: 16).

All embodiments described with respect to the different substances, uses and methods can be combined in any desired way and can be transferred to any other substance, use or method in any desired combination. Thereby, embodiments of substances can be transferred to uses and methods, embodiments of uses can be transferred to substances and methods, and embodiment of methods can be transferred to substances and uses.

BRIEF DESCRIPTION OF THE DRAWINGS

Aspect of the solution will be explained in more detail in the following making reference to exemplary embodiments and to accompanying Figures.

FIG. 3A shows a MALDI-TOF spectrum of MBP-fp-5 (10TAG);

DESCRIPTION OF THE INVENTION

First Exemplary Embodiment

Many generally known protecting groups can be used to produce a protected 3,4-dihydroxyphenylalanine derivative and thus to allow spatiotemporal activation of Dopa's adhesive properties.

An elegant strategy involves engineering the metabolism of bacterial cells in order to produce protected L-Dopa analogues from easily available, cheap precursor molecules. To convert these precursors into amino acids, recombinant strains can be created which express a novel engineered phenylalanine-ammonia lyase (PAL) or tyrosine-ammonia lyase (TAL).

O-pairs, e.g. based on MjTyrRS, are designed for in vivo tRNA aminoacylation with these protected L-Dopa derivatives. Deprotection can be achieved via different ways such as light-exposure or, as shown in the following reaction scheme 1, via acidic hydrolysis, finally leading to an underwater adhesive protein.

Reaction scheme 1: Protection of catechol functionality as isopropylidene with 2, 2-dimethoxypropone (DMP) introduced in tosylic acid (TsOH) to obtain a protected 3,4-dihydroxyphenylalanine derivative. After translation, the obtained peptide is posttranslationally deprotected by acidic hydrolysis to unmask the adhesive peptide.

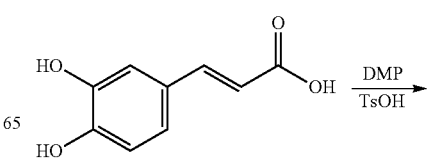

-continued

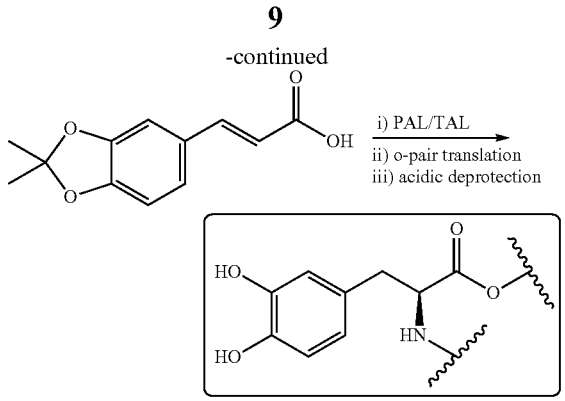

Second Exemplary Embodiment

ONB-Dopa was used as protected (photocaged) 3,4-dihydroxyphenylalanine derivative residue throughout this example.

To test whether multi-site incorporation of ONB-Dopa (to be more specifically, the ONB group was attached at the meta hydroxyl group of the catechol moiety; m-ONB-Dopa) into proteins naturally displaying high Dopa contents is feasible, a MAP type 5 (fp-5) was chosen as fp-5 is key component of the wet adhesion abilities of mussels. Fp-5 displays the highest Dopa contents of ~30 mol % which makes it especially attractive for multi-site incorporation of Dopa analogs. For expression tests, a fusion construct was used consisting of an N-terminal maltose binding protein (MBP) sequence with an additional TEV cleavage site and a C-terminal fp-5 sequence from *M. galloprovincialis* equipped with a $His_6$ tag.

Figure 1A:
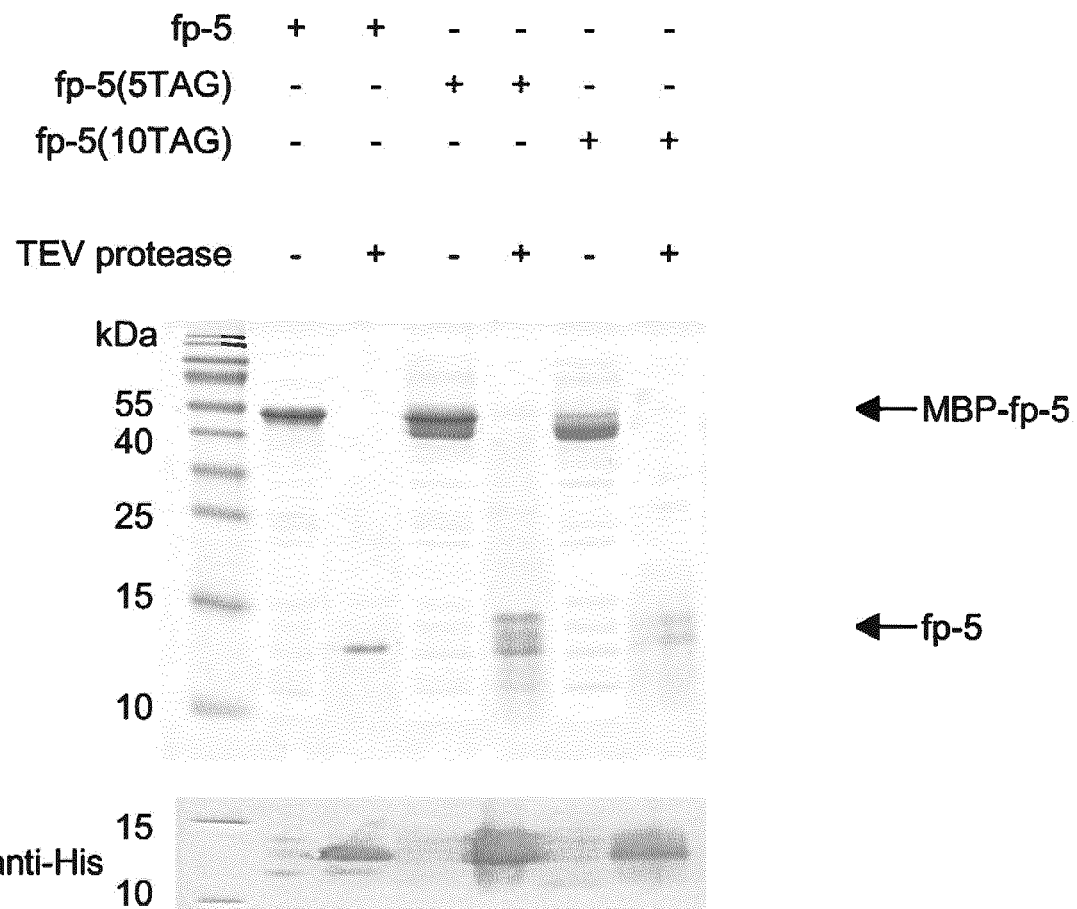
FIG. 1A shows an SDS-PAGE and Western Blot analysis of MBP-fp-5 variants expressed in B95.ΔA23.

Tyrosine codons were replaced at five or ten positions with amber codons to allow site-specific incorporation of m-ONB-Dopa by means of a novel ONB-Dopa-specific aaRS (ONB-DopaRS-1, SEQ ID NO: 8). For protein expression, the *E. coli* BL21(DE3) strain derivative B-95.ΔA23 was chosen, in which RF1 is eliminated. SDS-PAGE and Western blotting indicate the incorporation of m-ONB-Dopa into fp-5(5 amber codons; 5TAG) and fp-5(10 amber codons; 10TAG). The results are shown in FIG. 1A. WT MBP-fp-5 (lane 1), MBP-fp-5(5TAG) (lane 3), and MBP-fp-5(10TAG) (lane 5) were digested with TEV protease and insoluble fractions of fp-5 (lane 2), fp-5(5TAG) (lane 4), and fp-5(10TAG) (lane 6) were analyzed. Depending on the ONB-Dopa content, the expected molecular weight of MBP-fp-5 variants is ~51-54 kDa and ~10-12 kDa for fp-5 variants after TEV digest.

The occurrence of multiple bands of purified ONB-Dopa containing fp-5(5TAG) and fp-5(10TAG) variants in SDS PAGE analysis might be caused by partial reduction of the nitro group of ONB to an amine as previously reported.[21] Approximately ~6 mg $l^{-1}$ and ~1 mg $l^{-1}$ of purified fp-5 (5TAG) or fp-5(10TAG) were obtained in presence of m-ONB-Dopa, respectively, compared to ~18 mg $l^{-1}$ of wild-type (WT) fp-5 (containing 19 Tyr residues).

Figure 1B:
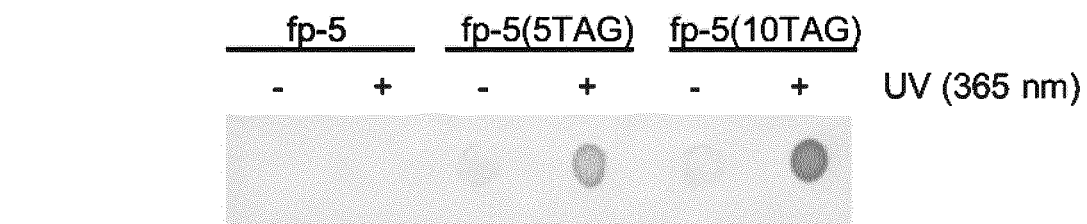
FIG. 1B shows an NBT staining of fp-5 variants expressed in presence of m-ONB-Dopa.

Production and decaging of fp-5(5TAG) and fp-5 (10TAG) variants bearing ONB-Dopa was verified after TEV digest by employing the redox-cycling nitro blue tetrazolium (NBT), which selectively stains Dopa or Dopa-quinone containing proteins.[22] While pronounced staining occurred in irradiated (+) Fp-5(5TAG) and Fp-5(10TAG) samples, with the latter showing stronger staining, almost no color development was observed without irradiation (−) (FIG. 1B). This indicates successful decaging of ONB-Dopa by UV irradiation.

Figure 1C:
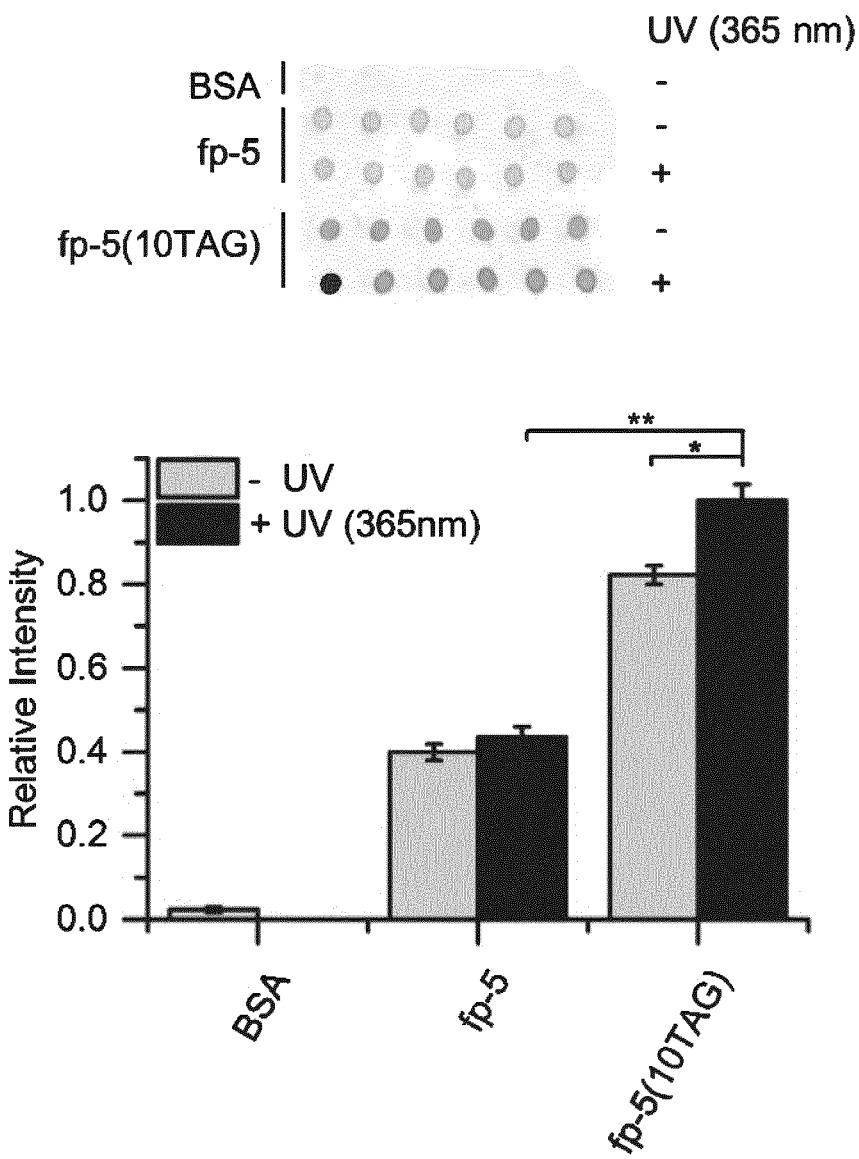
FIG. 1C shows a surface-coating analysis under dry conditions.

As a proof-of-principle test for Dopa-mediated adhesion, the surface adhesion ability of fp-5 variants was tested using a direct surface coating assay under dry conditions[11] (FIG. 1C). The upper panel of FIG. 1C shows an image of Coomassie-stained dots. Equal amounts of bovine serum albumin (BSA) and fp-5 variants were spotted at least six times with (+) or without (−) irradiation at 365 nm onto a polystyrene surface. The quantification of dot intensities shown in the lower panel of FIG. 1C indicates elevated adhesive potential after irradiation. The data represent mean±s.d.

The obtained data indicate elevated adhesion on polystyrene surfaces with increasing Dopa content after UV irradiation, demonstrating the adhesive potential of recombinantly produced photocaged mussel proteins. Taken together, these results show that ONB-DopaRS-1 facilitates efficient multi-site incorporation of ONB-Dopa into mussel protein fp-5, thus allowing recombinant production of photocaged MAPs with adhesive potential.

Figure 2:
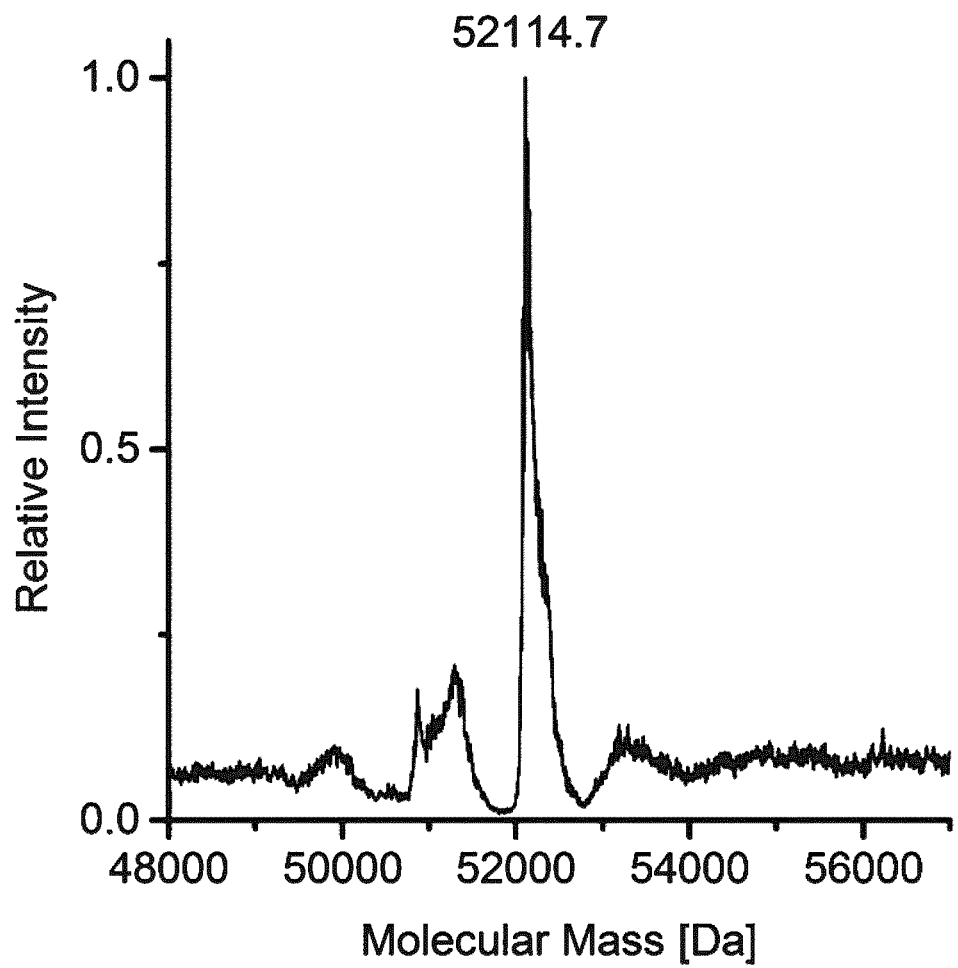
FIG. 2 shows a deconvoluted ESI-MS spectrum of MBP-fp-5(5TAG) after incorporation of m-ONB-Dopa.

The properties of the produced proteins were further analyzed by mass spectrometry (FIGS. 2 and 3). FIG. 2 shows a deconvoluted ESI-MS spectrum of MBP-fp-5 (5TAG) after incorporation of m-ONB-Dopa using ONB-YRS-1. The found and expected masses are as follows: MBP-fp-5 (5 ONB-Dopa), observed: 52114.7 Da, expected: 52115.8 Da.

Figure 3A:
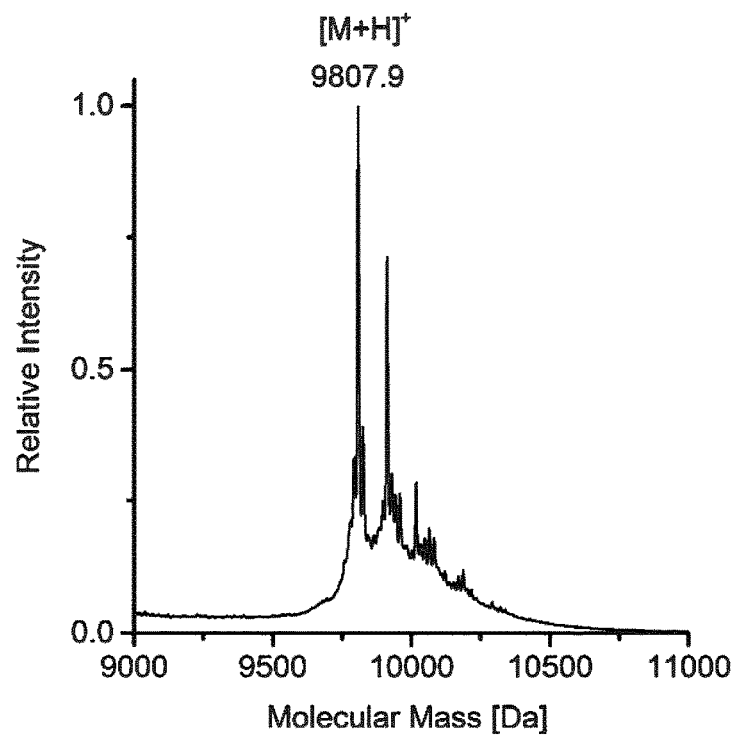
FIG. 3A shows a MALDI-TOF spectrum of MBP-fp-5 (5TAG)
Figure 3B:
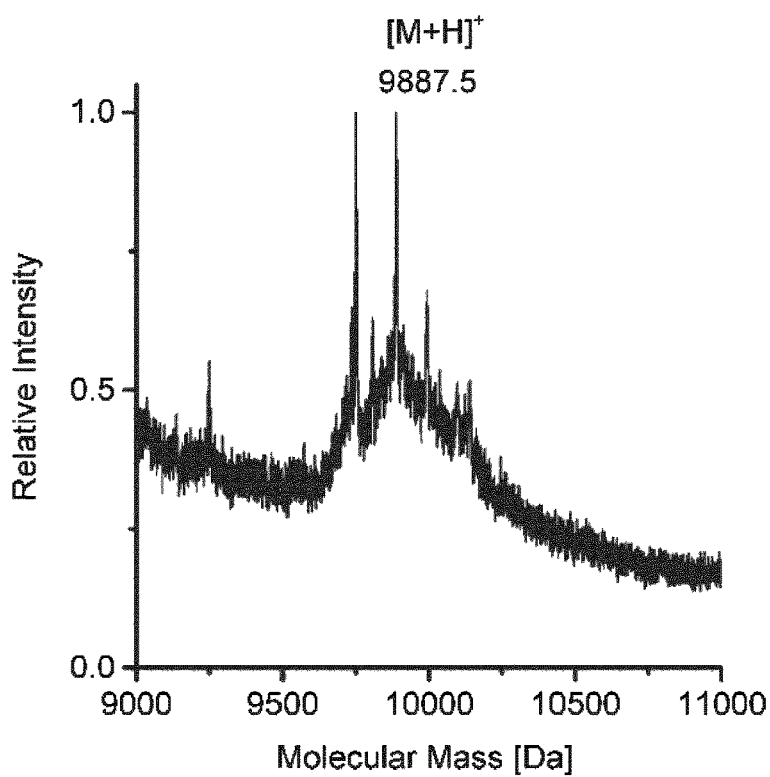

FIG. 3A shows a MALDI-TOF spectrum of MBP-fp-5 (5TAG) and FIG. 3B shows a MALDI-TOF spectrum of MBP-fp-5(10TAG) after incorporation of m-ONB-Dopa, TEV digest and irradiation with UV light. The found and expected masses are as follows: fp-5(5 Dopa), observed: 9807.9 Da (M+H$^+$), expected: 9807.7 Da (M+H$^+$). fp-5(10 Dopa), observed: 9887.5 Da (M+H$^+$), expected: 9887.7 Da (M+H$^+$).

In order to demonstrate the underwater adhesive potential of photocaged MAPs, atomic force microscopy (AFM) based force spectroscopy was employed which has been used to study Dopa-mediated wet adhesion. For this purpose, a bifunctional acetal-polyethylenglycol (PEG)-N-hydroxy-succinimide (NHS) linker molecule[24,25] allowed covalent attachment of MAPs via lysine residues.

Figure 4A:
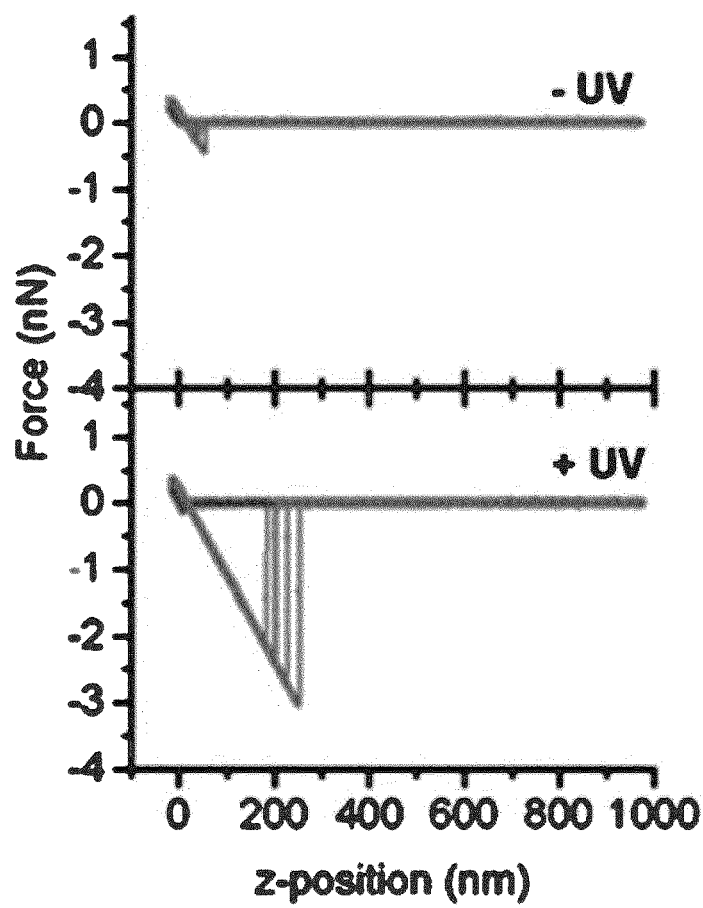
FIG. 4A shows F-D curves of fp-5(5TAG) interacting with a mica surface, obtained by an AFM analysis.
Figure 4B:
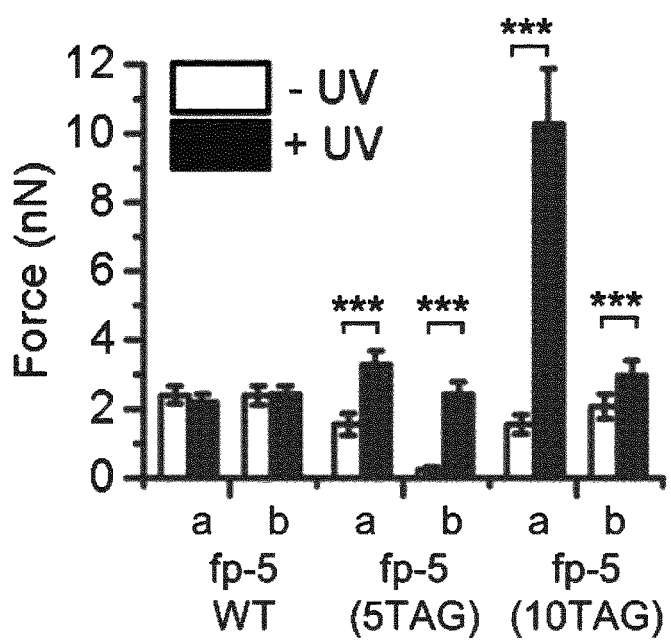
FIG. 4B shows force values of two functionalized tips with fp-5 WT and with fp-5(5TAG), obtained by AFM analysis.

Force-distance (F-D) curves of functionalized AFM tips were measured in sodium acetate buffer (10 mM, pH 4.6) on mica surfaces before and after irradiation with UV light (see FIGS. 4A and 4B). FIG. 4A depicts both approach and retraction signals. FIG. 4B shows force values of two tips (a, b) functionalized with different fp-5 variants (namely, fp-5 WT, fp-5(5TAG), and fp-5(10TAG)) before (white bars) and after irradiation (black bars). Data represent mean±s.d. of 100 F-D curves; significance is designated by symbols *$p<10^{-3}$, $p<10^{-6}$, *$p<10^{-6}$. While adhesion forces of fp-5 WT did not change significantly through UV irradiation in any measurement, fp-5(5TAG) and fp-5(10TAG) showed a significant increase of the adhesion force (up to 12-fold or up to 6.5-fold, respectively) upon UV light exposure.

To verify that Dopa accounts for the increased adhesion, unmodified and amino-functionalized tips were investigated. Both showed adhesion in the low pN range, in each case unaffected from UV light exposure. The data of fp-5 equipped with five or ten instances of m-ONB-Dopa provide clear evidence for the feasibility of spatiotemporal control of Dopa-mediated adhesion and the high potential of recombinantly produced photocaged MAPs.

LIST OF REFERENCES CITED IN THE PRECEDING SECTIONS OR BEING OTHERWISE OF RELEVANCE (1) Hoffmann, B.; Volkmer, E.; Kokott, A.; Augat, P.; Ohnmacht, M.; Sedlmayr, N.; Schieker, M.; Claes, L.; Mutschler, W.; Ziegler, G. *J. Mater. Sci. Mater. Med.* 2009, 20 (10), 2001.
(2) Donkerwolcke, M.; Burny, F.; Muster, D. *Biomaterials* 1998, 19 (16), 1461.
(3) Montanaro, L.; Arciola, C. R.; Cenni, E.; Ciapetti, G.; Savioli, F.; Filippini, F.; Barsanti, L. A. *Biomaterials* 2001, 22 (1), 59.
(4) Silverman, H. G.; Roberto, F. F. *Mar. Biotechnol.* 2007, 9 (6), 661.
(5) Stewart, R. J.; Ransom, T. C.; Hlady, V. J. *Polym. Sci. B. Polym. Phys.* 2011, 49 (11), 757.
(6) Waite, J. H. *Ann. N. Y. Acad. Sci.* 1999, 875, 301.
(7) Weber, S. C.; Chapman, M. W. *Clin. Orthop. Relat. Res.* 1984, No. 191, 249.
(8) Lee, H.; Dellatore, S. M.; Miller, W. M.; Messersmith, P. B. *Science* 2007, 318 (5849), 426.
(9) Lee, B. P.; Messersmith, P. B.; Israelachvili, J. N.; Waite, J. H. *Annu. Rev. Mater. Res.* 2011, 41 (1), 99.
(10) Hwang, D. S.; Gim, Y.; Yoo, H. J.; Cha, H. J. *Biomaterials* 2007, 28 (24), 3560.
(11) Yang, B.; Ayyadurai, N.; Yun, H.; Choi, Y. S.; Hwang, B. H.; Huang, J.; Lu, Q.; Zeng, H.; Cha, H. J. *Angew. Chem. Int. Ed. Engl.* 2014, 53 (49), 13360.
(12) Deiters, A.; Groff, D.; Ryu, Y.; Xie, J.; Schultz, P. G. *Angew. Chem. Int. Ed. Engl.* 2006, 45 (17), 2728.
(13) Arbely, E.; Torres-Kolbus, J.; Deiters, A.; Chin, J. W. *J. Am. Chem. Soc.* 2012, 134 (29), 11912.
(14) Luo, J.; Arbely, E.; Zhang, J.; Chou, C.; Uprety, R.; Chin, J. W.; Deiters, A. *Chem. Commun. (Camb).* 2016, 52 (55), 8529.
(15) Johnson, D. B. F.; Xu, J.; Shen, Z.; Takimoto, J. K.; Schultz, M. D.; Schmitz, R. J.; Xiang, Z.; Ecker, J. R.; Briggs, S. P.; Wang, L. *Nat. Chem. Biol.* 2011, 7 (11), 779.
(16) Lajoie, M. J.; Rovner, A. J.; Goodman, D. B.; Aerni, H.-R.; Haimovich, A. D.; Kuznetsov, G.; Mercer, J. A.; Wang, H. H.; Carr, P. A.; Mosberg, J. A.; Rohland, N.; Schultz, P. G.; Jacobson, J. M.; Rinehart, J.; Church, G. M.; Isaacs, F. J. *Science* 2013, 342 (6156), 357.
(17) Liu, C. C.; Schultz, P. G. *Annu. Rev. Biochem.* 2010, 79, 413.
(18) Wilkins, B. J.; Marionni, S.; Young, D. D.; Liu, J.; Wang, Y.; Di Salvo, M. L.; Deiters, A.; Cropp, T. A. *Biochemistry* 2010, 49 (8), 1557.
(19) Yu, J.; Wei, W.; Danner, E.; Ashley, R. K.; Israelachvili, J. N.; Waite, J. H. *Nat. Chem. Biol.* 2011, 7 (9), 588.
(20) Danner, E. W.; Kan, Y.; Hammer, M. U.; Israelachvili, J. N.; Waite, J. H. *Biochemistry* 2012, 51 (33), 6511.
(21) Nguyen, D. P.; Mahesh, M.; Elsässer, S. J.; Hancock, S. M.; Uttamapinant, C.; Chin, J. W. *J. Am. Chem. Soc.* 2014, 136 (6), 2240.
(22) Paz, M. A.; Flückiger, R.; Boak, A.; Kagan, H. M.; Gallop, P. M. *J. Biol. Chem.* 1991, 266 (2), 689.
(23) T. S. Young, I. Ahmad, J. A. Yin, P. G. Schultz, *J. Mol. Biol.* 2010, 395, 361-374.
(24) A. Ebner, L. Wildling, A. S. M. Kamruzzahan, C. Rankl, J. Wruss, C. D. Hahn, M. Hölzl, R. Zhu, F. Kienberger, D. Blaas, et al., *Bioconjug. Chem.* 2007, 18, 1176-84.
(25) L. Wildling, B. Unterauer, R. Zhu, A. Rupprecht, T. Haselgrübler, C. Rankl, A. Ebner, D. Vater, P. Pollheimer, E. E. Pohl, et al., *Bioconjug. Chem.* 2011, 22, 1239-48.

The invention claimed is:

1. A modified mussel adhesive foot protein-5 (fp-5), comprising a plurality of ortho-nitrobenzyl-3,4-dihydroxyphenylalanine residues, wherein each ortho-nitrobenzyl-3,4-dihydroxyphenylalanine residue comprises an ortho-nitrobenzyl group, wherein each ortho-nitrobenzyl-3,4-dihydroxyphenylalanine residue replaces a tyrosine residue and wherein the ortho-nitrobenzyl group can be cleaved from the ortho-nitrobenzyl-3,4-dihydroxyphenylalanine residue by irradiation with UV light,
wherein the modified mussel adhesive fp-5 comprises an amino acid sequence being at least 95% identical to SEQ ID NO: 1, SEQ ID NO: 2, SEQ ID NO: 3, SEQ ID NO: 11, SEQ ID NO: 12, or SEQ ID NO: 13.

2. The modified mussel adhesive protein according to claim 1, comprising an amino acid sequence being at least 95% identical to SEQ ID NO: 14, SEQ ID NO: 15, SEQ ID NO: 16, SEQ ID NO: 17, SEQ ID NO: 18, or SEQ ID NO: 19.

3. The modified mussel adhesive protein according to claim 2, comprising an amino acid sequence being at least 95% identical to SEQ ID NO: 4 that is fused to the N-terminus of the amino acid sequence defined in claim 2.

4. A nucleic acid encoding for a modified mussel adhesive protein according to claim 3, having a sequence being at least 99% identical to SEQ ID NO: 5, SEQ ID NO: 6 or SEQ ID NO: 7.

5. The modified mussel adhesive foot protein according to claim 1, wherein the modified mussel adhesive foot protein has the sequence of SEQ ID NO: 1.

6. The modified mussel adhesive foot protein according to claim 1, wherein the modified mussel adhesive foot protein has the sequence of SEQ ID NO: 2.

7. The modified mussel adhesive foot protein according to claim 1, wherein the modified mussel adhesive foot protein has the sequence of SEQ ID NO: 3.

8. The modified mussel adhesive foot protein according to claim 1, wherein the modified mussel adhesive foot protein has the sequence of SEQ ID NO: 11.

9. The modified mussel adhesive foot protein according to claim 1, wherein the modified mussel adhesive foot protein has the sequence of SEQ ID NO: 12.

10. The modified mussel adhesive foot protein according to claim 1, wherein the modified mussel adhesive foot protein has the sequence of SEQ ID NO: 13.

* * * * *

SEQUENCE LISTING

```
<160> NUMBER OF SEQ ID NOS: 19

<210> SEQ ID NO 1
<211> LENGTH: 83
<212> TYPE: PRT
<213> ORGANISM: Artificial Sequence
<220> FEATURE:
<223> OTHER INFORMATION: Contains 5 ONB-Dopa residues
<220> FEATURE:
<221> NAME/KEY: misc_feature
<222> LOCATION: (5)..(36)
<223> OTHER INFORMATION: Xaa is ortho-nitrobenzyl-3,4-
      dihydroxyphenylalanine

<400> SEQUENCE: 1

Ser Ser Glu Glu Xaa Lys Gly Gly Xaa Tyr Pro Gly Asn Ser Asn His
1               5                   10                  15

Xaa His Ser Gly Gly Ser Tyr His Gly Ser Gly Xaa His Gly Gly Tyr
            20                  25                  30

Lys Gly Lys Xaa Tyr Gly Lys Ala Lys Lys Tyr Tyr Tyr Lys Tyr Lys
        35                  40                  45

Asn Ser Gly Lys Tyr Lys Tyr Leu Lys Lys Ala Arg Lys Tyr His Arg
    50                  55                  60

Lys Gly Tyr Lys Lys Tyr Tyr Gly Gly Ser Ser Gly Ser His His His
65                  70                  75                  80

His His His
```

<210> SEQ ID NO 2
<211> LENGTH: 83
<212> TYPE: PRT
<213> ORGANISM: Artificial Sequence
<220> FEATURE:
<223> OTHER INFORMATION: Contains 10 ONB-Dopa residues
<220> FEATURE:
<221> NAME/KEY: MISC_FEATURE
<222> LOCATION: (5)..(71)
<223> OTHER INFORMATION: Xaa is ortho-nitrobenzyl-3,4-
      dihydroxyphenylalanine

<400> SEQUENCE: 2

Ser Ser Glu Glu Xaa Lys Gly Gly Xaa Tyr Pro Gly Asn Ser Asn His
1               5                   10                  15

Xaa His Ser Gly Gly Ser Tyr His Gly Ser Gly Xaa His Gly Gly Tyr
            20                  25                  30

Lys Gly Lys Xaa Tyr Gly Lys Ala Lys Lys Tyr Xaa Tyr Lys Xaa Lys
        35                  40                  45

Asn Ser Gly Lys Tyr Lys Xaa Leu Lys Lys Ala Arg Lys Tyr His Arg
    50                  55                  60

Lys Gly Xaa Lys Lys Tyr Xaa Gly Gly Ser Ser Gly Ser His His His
65                  70                  75                  80

His His His

<210> SEQ ID NO 3
<211> LENGTH: 83
<212> TYPE: PRT
<213> ORGANISM: Artificial Sequence
<220> FEATURE:
<223> OTHER INFORMATION: Contains 19 ONB-Dopa residues
<220> FEATURE:
<221> NAME/KEY: MISC_FEATURE
<222> LOCATION: (5)..(71)
<223> OTHER INFORMATION: Xaa is ortho-nitrobenzyl-3,4-
      dihydroxyphenylalanine

<400> SEQUENCE: 3

Ser Ser Glu Glu Xaa Lys Gly Gly Xaa Xaa Pro Gly Asn Ser Asn His
1               5                   10                  15

Xaa His Ser Gly Gly Ser Xaa His Gly Ser Gly Xaa His Gly Gly Xaa
            20                  25                  30

Lys Gly Lys Xaa Xaa Gly Lys Ala Lys Lys Xaa Xaa Lys Xaa Xaa Lys
        35                  40                  45

Asn Ser Gly Lys Xaa Lys Xaa Leu Lys Lys Ala Arg Lys Xaa His Arg
    50                  55                  60

Lys Gly Xaa Lys Lys Xaa Xaa Gly Gly Ser Ser Gly Ser His His His
65                  70                  75                  80

His His His

<210> SEQ ID NO 4
<211> LENGTH: 381
<212> TYPE: PRT
<213> ORGANISM: Artificial Sequence
<220> FEATURE:
<223> OTHER INFORMATION: Maltose binding protein and TEV cleavage site

<400> SEQUENCE: 4

Met Ala Gly Lys Ile Glu Glu Gly Lys Leu Val Ile Trp Ile Asn Gly
1               5                   10                  15

Asp Lys Gly Tyr Asn Gly Leu Ala Glu Val Gly Lys Lys Phe Glu Lys
        20                  25                  30

Asp Thr Gly Ile Lys Val Thr Val Glu His Pro Asp Lys Leu Glu Glu
        35                  40                  45

Lys Phe Pro Gln Val Ala Ala Thr Gly Asp Gly Pro Asp Ile Ile Phe
50                  55                  60

Trp Ala His Asp Arg Phe Gly Gly Tyr Ala Gln Ser Gly Leu Leu Ala
65                  70                  75                  80

Glu Ile Thr Pro Asp Lys Ala Phe Gln Asp Lys Leu Tyr Pro Phe Thr
                85                  90                  95

Trp Asp Ala Val Arg Tyr Asn Gly Lys Leu Ile Ala Tyr Pro Ile Ala
            100                 105                 110

Val Glu Ala Leu Ser Leu Ile Tyr Asn Lys Asp Leu Leu Pro Asn Pro
        115                 120                 125

Pro Lys Thr Trp Glu Glu Ile Pro Ala Leu Asp Lys Glu Leu Lys Ala
130                 135                 140

Lys Gly Lys Ser Ala Leu Met Phe Asn Leu Gln Glu Pro Tyr Phe Thr
145                 150                 155                 160

Trp Pro Leu Ile Ala Ala Asp Gly Gly Tyr Ala Phe Lys Tyr Glu Asn
                165                 170                 175

Gly Lys Tyr Asp Ile Lys Asp Val Gly Val Asp Asn Ala Gly Ala Lys
            180                 185                 190

Ala Gly Leu Thr Phe Leu Val Asp Leu Ile Lys Asn Lys His Met Asn
        195                 200                 205

Ala Asp Thr Asp Tyr Ser Ile Ala Glu Ala Ala Phe Asn Lys Gly Glu
210                 215                 220

Thr Ala Met Thr Ile Asn Gly Pro Trp Ala Trp Ser Asn Ile Asp Thr
225                 230                 235                 240

Ser Lys Val Asn Tyr Gly Val Thr Val Leu Pro Thr Phe Lys Gly Gln
                245                 250                 255

Pro Ser Lys Pro Phe Val Gly Val Leu Ser Ala Gly Ile Asn Ala Ala
            260                 265                 270

Ser Pro Asn Lys Glu Leu Ala Lys Glu Phe Leu Glu Asn Tyr Leu Leu
        275                 280                 285

Thr Asp Glu Gly Leu Glu Ala Val Asn Lys Asp Lys Pro Leu Gly Ala
290                 295                 300

Val Ala Leu Lys Ser Tyr Glu Glu Glu Leu Ala Lys Asp Pro Arg Ile
305                 310                 315                 320

Ala Ala Thr Met Glu Asn Ala Gln Lys Gly Glu Ile Met Pro Asn Ile
                325                 330                 335

Pro Gln Met Ser Ala Phe Trp Tyr Ala Val Arg Thr Ala Val Ile Asn
            340                 345                 350

Ala Ala Ser Gly Arg Gln Thr Val Asp Glu Ala Leu Lys Asp Ala Gln
        355                 360                 365

Thr Asn Ser Ser Ser Gly Ser Glu Asn Leu Tyr Phe Gln
370                 375                 380

<210> SEQ ID NO 5
<211> LENGTH: 1395
<212> TYPE: DNA
<213> ORGANISM: Artificial Sequence
<220> FEATURE:
<223> OTHER INFORMATION: Contains 5 in-frame TAG sites

<400> SEQUENCE: 5

```
atggccggca aaatcgaaga aggtaaactg gtaatctgga ttaacggcga taaaggctat       60
aacggtctcg ctgaagtcgg taagaaattc gagaaagata ccggaattaa agtcaccgtt      120
gagcatccgg ataaactgga agagaaattc ccacaggttg cggcaactgg cgatggccct      180
gacattatct tctgggcaca cgaccgcttt ggtggctacg ctcaatctgg cctgttggct      240
gaaatcaccc cggacaaagc gttccaggac aagctgtatc cgtttacctg ggatgccgta      300
cgttacaacg gcaagctgat tgcttacccg atcgctgttg aagcgttatc gctgatttat      360
aacaaagatc tgctgccgaa cccgccaaaa acctgggaag atcccggc gctggataaa        420
gaactgaaag cgaaaggtaa gagcgcgctg atgttcaacc tgcaagaacc gtacttcacc      480
tggccgctga ttgctgctga cggggggttat gcgttcaagt atgaaaacgg caagtacgac      540
attaagacg tgggcgtgga taacgctggc gcgaaagcgg tctgaccttt cctggttgac       600
ctgattaaaa acaaacacat gaatgcagac accgattact ccatcgcaga agctgccttt      660
aataaaggcg aaacagcgat gaccatcaac ggcccgtggg catggtccaa catcgacacc      720
agcaaagtga attatggtgt aacggtactg ccgaccttca agggtcaacc atccaaaccg      780
ttcgttggcg tgctgagcgc aggtattaac gccgccagtc cgaacaaaga gctggcaaaa      840
gagttcctcg aaaactatct gctgactgat gaaggtctgg aagcggttaa taaagacaaa      900
ccgctgggtg ccgtagcgct gaagtcttac gaggaagagt tggcgaaaga tccacgtatt      960
gccgccacca tggaaaacgc ccagaaaggt gaaatcatgc cgaacatccc gcagatgtcc     1020
gctttctggt atgccgtgcg tactgcggtg atcaacgccg ccagcggtcg tcagactgtc     1080
gatgaagccc tgaaagacgc gcagactaat tcgagctcgg gcagcgagaa cctgtacttc     1140
caaagcagcg aagaatagaa aggtggttag tatccgggta acagcaacca ttagcatagc     1200
ggtggtagct atcatggtag cggttagcat ggtggttata aggtaaata gtatggcaaa      1260
gccaaaaaat actactacaa atacaaaaac agcgggaaat acaaatatct gaaaaaagcc     1320
cgtaaatatc atcgtaaagg ctacaaaaaa tactatggtg gcagcagcgg cagccatcat     1380
catcatcatc actaa                                                      1395
```

<210> SEQ ID NO 6
<211> LENGTH: 1395
<212> TYPE: DNA
<213> ORGANISM: Artificial Sequence
<220> FEATURE:
<223> OTHER INFORMATION: Contains 10 in-frame TAG sites

<400> SEQUENCE: 6

```
atggccggca aaatcgaaga aggtaaactg gtaatctgga ttaacggcga taaaggctat       60
aacggtctcg ctgaagtcgg taagaaattc gagaaagata ccggaattaa agtcaccgtt      120
gagcatccgg ataaactgga agagaaattc ccacaggttg cggcaactgg cgatggccct      180
gacattatct tctgggcaca cgaccgcttt ggtggctacg ctcaatctgg cctgttggct      240
gaaatcaccc cggacaaagc gttccaggac aagctgtatc cgtttacctg ggatgccgta      300
cgttacaacg gcaagctgat tgcttacccg atcgctgttg aagcgttatc gctgatttat      360
aacaaagatc tgctgccgaa cccgccaaaa acctgggaag atcccggc gctggataaa        420
gaactgaaag cgaaaggtaa gagcgcgctg atgttcaacc tgcaagaacc gtacttcacc      480
tggccgctga ttgctgctga cggggggttat gcgttcaagt atgaaaacgg caagtacgac      540
```

```
attaaagacg tgggcgtgga taacgctggc gcgaaagcgg gtctgacctt cctggttgac    600
ctgattaaaa acaaacacat gaatgcagac accgattact ccatcgcaga agctgccttt    660
aataaaggcg aaacagcgat gaccatcaac ggcccgtggg catggtccaa catcgacacc    720
agcaaagtga attatggtgt aacggtactg ccgaccttca agggtcaacc atccaaaccg    780
ttcgttggcg tgctgagcgc aggtattaac gccgccagtc cgaacaaaga gctggcaaaa    840
gagttcctcg aaaactatct gctgactgat gaaggtctgg aagcggttaa taaagacaaa    900
ccgctgggtg ccgtagcgct gaagtcttac gaggaagagt tggcgaaaga tccacgtatt    960
gccgccacca tggaaaacgc ccagaaaggt gaaatcatgc gaacatccc gcagatgtcc   1020 gctttctggt atgccgtgcg tactgcggtg atcaacgccg ccagcggtcg tcagactgtc   1080
gatgaagccc tgaaagacgc gcagactaat tcgagctcgg gcagcgagaa cctgtacttc   1140
caaagcagcg aagaatagaa aggtggttag tatccgggta acagcaacca ttagcatagc   1200
ggtggtagct atcatggtag cggttagcat ggtggttata aggtaaata gtatggcaaa   1260 gccaaaaaat actagtacaa atagaaaaac agcgggaaat acaaatagct gaaaaaagcc   1320
cgtaaatatc atcgtaaagg ctagaaaaaa tactagggtg gcagcagcgg cagccatcat   1380
catcatcatc actaa                                                    1395

<210> SEQ ID NO 7
<211> LENGTH: 1395
<212> TYPE: DNA
<213> ORGANISM: Artificial Sequence
<220> FEATURE:
<223> OTHER INFORMATION: Contains 19 in-frame TAG sites

<400> SEQUENCE: 7
atggccggca aaatcgaaga aggtaaactg gtaatctgga ttaacggcga taaaggctat     60
aacggtctcg ctgaagtcgg taagaaattc gagaaagata ccggaattaa agtcaccgtt    120
gagcatccgg ataaactgga agagaaattc ccacaggttg cggcaactgg cgatggccct    180
gacattatct tctgggcaca cgaccgcttt ggtggctacg ctcaatctgg cctgttggct    240
gaaatcaccc cggacaaagc gttccaggac aagctgtatc cgtttacctg ggatgccgta    300
cgttacaacg gcaagctgat tgcttaccc atcgctgttg aagcgttatc gctgatttat    360
aacaaagatc tgctgccgaa cccgccaaaa acctgggaag agatcccggc gctggataaa    420
gaactgaaag cgaaaggtaa gagcgcgctg atgttcaacc tgcaagaacc gtacttcacc    480
tggccgctga ttgctgctga cggggggttat gcgttcaagt atgaaaacgg caagtacgac    540
attaaagacg tgggcgtgga taacgctggc gcgaaagcgg gtctgacctt cctggttgac    600
ctgattaaaa acaaacacat gaatgcagac accgattact ccatcgcaga agctgccttt    660
aataaaggcg aaacagcgat gaccatcaac ggcccgtggg catggtccaa catcgacacc    720
agcaaagtga attatggtgt aacggtactg ccgaccttca agggtcaacc atccaaaccg    780
ttcgttggcg tgctgagcgc aggtattaac gccgccagtc cgaacaaaga gctggcaaaa    840
gagttcctcg aaaactatct gctgactgat gaaggtctgg aagcggttaa taaagacaaa    900
ccgctgggtg ccgtagcgct gaagtcttac gaggaagagt tggcgaaaga tccacgtatt    960
gccgccacca tggaaaacgc ccagaaaggt gaaatcatgc gaacatccc gcagatgtcc   1020 gctttctggt atgccgtgcg tactgcggtg atcaacgccg ccagcggtcg tcagactgtc   1080
gatgaagccc tgaaagacgc gcagactaat tcgagctcgg gcagcgagaa cctgtacttc   1140
caaagcagcg aagaatagaa aggtggttag tagccgggta acagcaacca ttagcatagc   1200
```

```
ggtggtagct agcatggtag cggttagcat ggtggttaga aaggtaaata gtagggcaaa    1260
gccaaaaaat agtagtagaa atagaaaaac agcgggaaat agaaatagct gaaaaaagcc    1320
cgtaaatagc atcgtaaagg ctagaaaaaa tagtagggtg gcagcagcgg cagccatcat    1380
catcatcatc actaa                                                    1395
```

<210> SEQ ID NO 8
<211> LENGTH: 306
<212> TYPE: PRT
<213> ORGANISM: Artificial Sequence
<220> FEATURE:
<223> OTHER INFORMATION: ONB-Dopa aminoacyl-tRNA synthetase 1

<400> SEQUENCE: 8

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Ile Leu Ala Asp Leu Ala Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Ala Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Ala Ala His
145                 150                 155                 160

Tyr Met Gly Val Asp Val Asn Val Gly Gly Met Glu Gln Arg Lys Ile
                165                 170                 175

His Met Leu Gln Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Arg Leu Lys
        275                 280                 285

Asn Ala Val Ala Glu Glu Leu Ile Lys Ile Leu Glu Pro Ile Arg Lys
    290                 295                 300

Arg Leu
305
```

<210> SEQ ID NO 9
<211> LENGTH: 306
<212> TYPE: PRT
<213> ORGANISM: Artificial Sequence
<220> FEATURE:
<223> OTHER INFORMATION: ONB-Dopa aminoacyl-tRNA synthetase 2

<400> SEQUENCE: 9

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ser
                20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
        50                  55                  60

Ile Leu Ala Asp Leu Ala Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Ala Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Ala Gly His
145                 150                 155                 160

Tyr Met Gly Ala Asp Val Asn Val Gly Gly Met Glu Gln Arg Lys Ile
                165                 170                 175

His Met Leu Gln Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Arg Leu Lys
        275                 280                 285

Asn Ala Val Ala Glu Glu Leu Ile Lys Ile Leu Glu Pro Ile Arg Lys
    290                 295                 300

Arg Leu
305
```

<210> SEQ ID NO 10
<211> LENGTH: 306
<212> TYPE: PRT
<213> ORGANISM: Artificial Sequence
<220> FEATURE:
<223> OTHER INFORMATION: ONB-Dopa aminoacyl-tRNA synthetase 3

<400> SEQUENCE: 10

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ser
            20                  25                  30

Ile Gly Phe Glu Pro Ser Gly Lys Ile His Leu Gly Tyr Leu Gln
        35                  40                  45

Ile Lys Lys Met Ile Asp Leu Gln Asn Ala Gly Phe Asp Ile Ile Ile
    50                  55                  60

Ile Leu Ala Asp Leu Ala Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Ala Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Ala Gly His
145                 150                 155                 160

Tyr Met Gly Val Asp Val Ser Val Gly Met Glu Gln Arg Lys Ile
                165                 170                 175

His Met Leu Gln Arg Glu Leu Leu Pro Lys Lys Gln Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Arg Leu Lys
        275                 280                 285

Asn Ala Val Ala Glu Glu Leu Ile Lys Ile Leu Glu Pro Ile Arg Lys
290                 295                 300

Arg Leu
305

<210> SEQ ID NO 11
<211> LENGTH: 77
<212> TYPE: PRT
<213> ORGANISM: Artificial Sequence
<220> FEATURE:
<223> OTHER INFORMATION: Contains 5 ONB-Dopa residues
<220> FEATURE:
<221> NAME/KEY: MISC_FEATURE
<222> LOCATION: (5)..(36)
<223> OTHER INFORMATION: Xaa is ortho-nitrobenzyl-3,4-
      dihydroxyphenylalanine

<400> SEQUENCE: 11

Ser Ser Glu Glu Xaa Lys Gly Gly Xaa Tyr Pro Gly Asn Ser Asn His
1               5                   10                  15

Xaa His Ser Gly Gly Ser Tyr His Gly Ser Gly Xaa His Gly Gly Tyr
            20                  25                  30

Lys Gly Lys Xaa Tyr Gly Lys Ala Lys Lys Tyr Tyr Lys Tyr Lys
        35                  40                  45

Asn Ser Gly Lys Tyr Lys Tyr Leu Lys Lys Ala Arg Lys Tyr His Arg
    50                  55                  60

Lys Gly Tyr Lys Lys Tyr Tyr Gly Gly Ser Ser Gly Ser
65                  70                  75

<210> SEQ ID NO 12
<211> LENGTH: 77
<212> TYPE: PRT
<213> ORGANISM: Artificial Sequence
<220> FEATURE:
<223> OTHER INFORMATION: Contains 10 ONB-Dopa residues
<220> FEATURE:
<221> NAME/KEY: MISC_FEATURE
<222> LOCATION: (5)..(71)
<223> OTHER INFORMATION: Xaa is ortho-nitrobenzyl-3,4-
      dihydroxyphenylalanine

<400> SEQUENCE: 12

Ser Ser Glu Glu Xaa Lys Gly Gly Xaa Tyr Pro Gly Asn Ser Asn His
1               5                   10                  15

Xaa His Ser Gly Gly Ser Tyr His Gly Ser Gly Xaa His Gly Gly Tyr
            20                  25                  30

Lys Gly Lys Xaa Tyr Gly Lys Ala Lys Lys Tyr Xaa Tyr Lys Xaa Lys
        35                  40                  45

Asn Ser Gly Lys Tyr Lys Xaa Leu Lys Lys Ala Arg Lys Tyr His Arg
    50                  55                  60

Lys Gly Xaa Lys Lys Tyr Xaa Gly Gly Ser Ser Gly Ser
65                  70                  75

<210> SEQ ID NO 13
<211> LENGTH: 77
<212> TYPE: PRT
<213> ORGANISM: Artificial Sequence
<220> FEATURE:
<223> OTHER INFORMATION: Contains 19 ONB-Dopa residues
<220> FEATURE:
<221> NAME/KEY: MISC_FEATURE
<222> LOCATION: (5)..(71)
<223> OTHER INFORMATION: Xaa is ortho-nitrobenzyl-3,4-
      dihydroxyphenylalanine

<400> SEQUENCE: 13

Ser Ser Glu Glu Xaa Lys Gly Gly Xaa Xaa Pro Gly Asn Ser Asn His
1               5                   10                  15

Xaa His Ser Gly Gly Ser Xaa His Gly Ser Gly Xaa His Gly Gly Xaa
            20                  25                  30

Lys Gly Lys Xaa Xaa Gly Lys Ala Lys Lys Xaa Xaa Xaa Lys Xaa Lys
        35                  40                  45

Asn Ser Gly Lys Xaa Lys Xaa Leu Lys Lys Ala Arg Lys Xaa His Arg
    50                  55                  60

Lys Gly Xaa Lys Lys Xaa Xaa Gly Gly Ser Ser Gly Ser
65                  70                  75

```
<210> SEQ ID NO 14
<211> LENGTH: 83
<212> TYPE: PRT
<213> ORGANISM: Artificial Sequence
<220> FEATURE:
<223> OTHER INFORMATION: Contains 5 photocaged Dopa residues
<220> FEATURE:
<221> NAME/KEY: MISC_FEATURE
<222> LOCATION: (5)..(36)
<223> OTHER INFORMATION: Xaa is a photocaged 3,4-dihydroxyphenylalanine

<400> SEQUENCE: 14

Ser Ser Glu Glu Xaa Lys Gly Gly Xaa Tyr Pro Gly Asn Ser Asn His
1               5                   10                  15

Xaa His Ser Gly Gly Ser Tyr His Gly Ser Gly Xaa His Gly Gly Tyr
            20                  25                  30

Lys Gly Lys Xaa Tyr Gly Lys Ala Lys Lys Tyr Tyr Tyr Lys Tyr Lys
        35                  40                  45

Asn Ser Gly Lys Tyr Lys Tyr Leu Lys Lys Ala Arg Lys Tyr His Arg
    50                  55                  60

Lys Gly Tyr Lys Lys Tyr Tyr Gly Gly Ser Ser Gly Ser His His His
65                  70                  75                  80

His His His

<210> SEQ ID NO 15
<211> LENGTH: 83
<212> TYPE: PRT
<213> ORGANISM: Artificial Sequence
<220> FEATURE:
<223> OTHER INFORMATION: Contains 10 photocaged Dopa residues
<220> FEATURE:
<221> NAME/KEY: MISC_FEATURE
<222> LOCATION: (5)..(71)
<223> OTHER INFORMATION: Xaa is a photocaged 3,4-dihydroxyphenylalanine

<400> SEQUENCE: 15

Ser Ser Glu Glu Xaa Lys Gly Gly Xaa Tyr Pro Gly Asn Ser Asn His
1               5                   10                  15

Xaa His Ser Gly Gly Ser Tyr His Gly Ser Gly Xaa His Gly Gly Tyr
            20                  25                  30

Lys Gly Lys Xaa Tyr Gly Lys Ala Lys Lys Tyr Xaa Tyr Lys Xaa Lys
        35                  40                  45

Asn Ser Gly Lys Tyr Lys Xaa Leu Lys Lys Ala Arg Lys Tyr His Arg
    50                  55                  60

Lys Gly Xaa Lys Lys Tyr Xaa Gly Gly Ser Ser Gly Ser His His His
65                  70                  75                  80

His His His

<210> SEQ ID NO 16
<211> LENGTH: 83
<212> TYPE: PRT
<213> ORGANISM: Artificial Sequence
<220> FEATURE:
<223> OTHER INFORMATION: Contains 19 photocaged Dopa residues
<220> FEATURE:
<221> NAME/KEY: MISC_FEATURE
<222> LOCATION: (5)..(71)
<223> OTHER INFORMATION: Xaa is a photocaged 3,4-dihydroxyphenylalanine

<400> SEQUENCE: 16

Ser Ser Glu Glu Xaa Lys Gly Gly Xaa Xaa Pro Gly Asn Ser Asn His
1               5                   10                  15
```

Xaa His Ser Gly Gly Ser Xaa His Gly Ser Gly Xaa His Gly Gly Xaa
            20                  25                  30

Lys Gly Lys Xaa Xaa Gly Lys Ala Lys Lys Xaa Xaa Xaa Lys Xaa Lys
        35                  40                  45

Asn Ser Gly Lys Xaa Lys Xaa Leu Lys Lys Ala Arg Lys Xaa His Arg
    50                  55                  60

Lys Gly Xaa Lys Lys Xaa Xaa Gly Gly Ser Ser Gly Ser His His His
65                  70                  75                  80

His His His

<210> SEQ ID NO 17
<211> LENGTH: 77
<212> TYPE: PRT
<213> ORGANISM: Artificial Sequence
<220> FEATURE:
<223> OTHER INFORMATION: Contains 5 photocaged Dopa residues
<220> FEATURE:
<221> NAME/KEY: MISC_FEATURE
<222> LOCATION: (5)..(36)
<223> OTHER INFORMATION: Xaa is a photocaged 3,4-dihydroxyphenylalanine

<400> SEQUENCE: 17

Ser Ser Glu Glu Xaa Lys Gly Gly Xaa Tyr Pro Gly Asn Ser Asn His
1               5                   10                  15

Xaa His Ser Gly Gly Ser Tyr His Gly Ser Gly Xaa His Gly Gly Tyr
            20                  25                  30

Lys Gly Lys Xaa Tyr Gly Lys Ala Lys Lys Tyr Tyr Tyr Lys Tyr Lys
        35                  40                  45

Asn Ser Gly Lys Tyr Lys Tyr Leu Lys Lys Ala Arg Lys Tyr His Arg
    50                  55                  60

Lys Gly Tyr Lys Lys Tyr Tyr Gly Gly Ser Ser Gly Ser
65                  70                  75

<210> SEQ ID NO 18
<211> LENGTH: 77
<212> TYPE: PRT
<213> ORGANISM: Artificial Sequence
<220> FEATURE:
<223> OTHER INFORMATION: Contains 10 photocaged Dopa residues
<220> FEATURE:
<221> NAME/KEY: MISC_FEATURE
<222> LOCATION: (5)..(71)
<223> OTHER INFORMATION: Xaa is a photocaged 3,4-dihydroxyphenylalanine

<400> SEQUENCE: 18

Ser Ser Glu Glu Xaa Lys Gly Gly Xaa Tyr Pro Gly Asn Ser Asn His
1               5                   10                  15

Xaa His Ser Gly Gly Ser Tyr His Gly Ser Gly Xaa His Gly Gly Tyr
            20                  25                  30

Lys Gly Lys Xaa Tyr Gly Lys Ala Lys Lys Tyr Xaa Tyr Lys Xaa Lys
        35                  40                  45

Asn Ser Gly Lys Tyr Lys Xaa Leu Lys Lys Ala Arg Lys Tyr His Arg
    50                  55                  60

Lys Gly Xaa Lys Lys Tyr Xaa Gly Gly Ser Ser Gly Ser
65                  70                  75

<210> SEQ ID NO 19
<211> LENGTH: 77
<212> TYPE: PRT
<213> ORGANISM: Artificial Sequence
<220> FEATURE:

```
<223> OTHER INFORMATION: Contains 19 photocaged Dopa residues
<220> FEATURE:
<221> NAME/KEY: MISC_FEATURE
<222> LOCATION: (5)..(71)
<223> OTHER INFORMATION: Xaa is a photocaged 3,4-dihydroxyphenylalanine

<400> SEQUENCE: 19

Ser Ser Glu Glu Xaa Lys Gly Gly Xaa Xaa Pro Gly Asn Ser Asn His
1               5                   10                  15

Xaa His Ser Gly Gly Ser Xaa His Gly Ser Gly Xaa His Gly Gly Xaa
            20              25                  30

Lys Gly Lys Xaa Xaa Gly Lys Ala Lys Lys Xaa Xaa Xaa Lys Xaa Lys
        35                  40                  45

Asn Ser Gly Lys Xaa Lys Xaa Leu Lys Lys Ala Arg Lys Xaa His Arg
    50              55                  60

Lys Gly Xaa Lys Lys Xaa Xaa Gly Gly Ser Ser Gly Ser
65              70                  75
```